United States Patent [19]

McKinnon

[11] Patent Number: 4,572,210

[45] Date of Patent: Feb. 25, 1986

[54] SYRINGE WITH MEANS FOR ALLOWING PASSAGE OF AIR WHILE PREVENTING THE PASSAGE OF BLOOD TO OBTAIN A GAS-FREE BLOOD SAMPLE

[75] Inventor: Robert J. McKinnon, Franktown, Colo.

[73] Assignee: Marquest Medical Products, Inc., Englewood, Colo.

[21] Appl. No.: 359,292

[22] Filed: Mar. 18, 1982

Related U.S. Application Data

[63] Continuation of Ser. No. 279,453, Jul. 1, 1981, abandoned.

[51] Int. Cl.$^4$ ............................................. A61B 5/00
[52] U.S. Cl. .................................... 128/765; 604/190
[58] Field of Search ............................... 128/762–766, 128/218 P, 218 PA, 218 R, 760; 210/323 R, 474, 477, 482; 604/190, 187

[56] References Cited

U.S. PATENT DOCUMENTS

| | | | |
|---|---|---|---|
| 1,643,531 | 9/1927 | Wolf . | |
| 3,291,128 | 12/1966 | O'Neil | 128/218 |
| 3,656,480 | 4/1972 | Rubricius | 128/218 |
| 3,736,932 | 6/1973 | Satchell | 128/218 |
| 3,809,298 | 5/1974 | Harris, Sr. et al. | 222/386 |
| 3,864,979 | 2/1975 | Ayres | 73/425.4 |
| 3,886,930 | 6/1975 | Ryan | 128/2 |
| 3,938,513 | 2/1976 | Hargest | 128/218 |
| 3,960,139 | 6/1976 | Bailey | 128/2 |
| 3,978,846 | 9/1976 | Bailey | 128/2 |
| 4,008,718 | 2/1977 | Pitesky | 128/218 |
| 4,016,879 | 4/1977 | Mellor | 128/214.4 |
| 4,057,052 | 11/1977 | Kaufman et al. | 128/2 |
| 4,206,768 | 6/1980 | Bailey | 128/763 |
| 4,207,870 | 6/1980 | Eldridge | 128/766 |
| 4,266,558 | 5/1981 | Akhavi | 128/766 |
| 4,266,559 | 5/1981 | Akhavi | 128/766 |
| 4,327,745 | 5/1982 | Ford, Jr. | 128/765 |
| 4,340,067 | 7/1982 | Rattenborg | 128/763 |

Primary Examiner—John D. Yasko
Attorney, Agent, or Firm—Sheridan, Ross & McIntosh

[57] ABSTRACT

A syringe device for obtaining a gas-free blood sample has a tubular body connected to an hypodermic needle. The tubular body receives a resilient sealing member operatively connected to a plunger rod. The sealing member and plunger rod have a vent formed longitudinally therealong to provide a passageway for the purge of air as an interior chamber of the tubular body is filled with blood. The passageway is covered with an hydrophobic filter allowing the passage of air until such time as blood completely contacts the filter, at which time blood cannot cross the hydrophobic filter. The interior chamber containing the blood sample is then purged of all air.

44 Claims, 5 Drawing Figures

U.S. Patent     Feb. 25, 1986     4,572,210
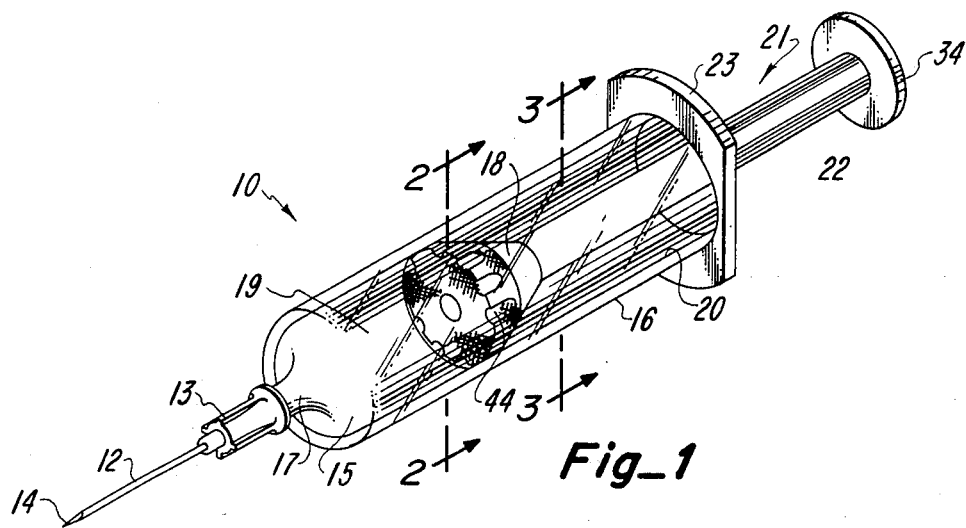
Fig_1
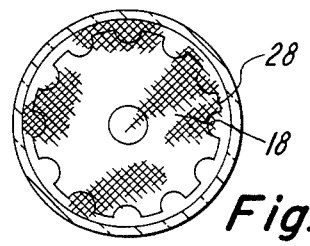
Fig_2
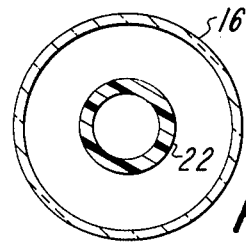
Fig_3
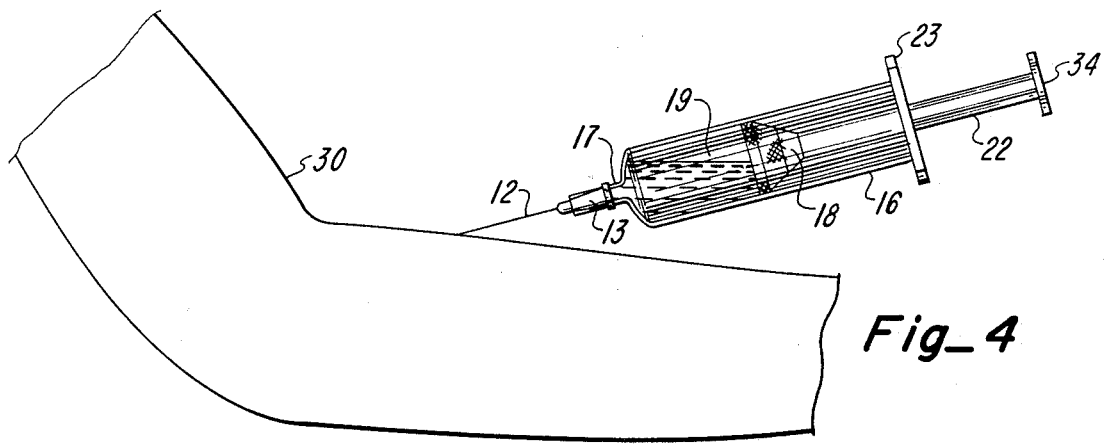
Fig_4
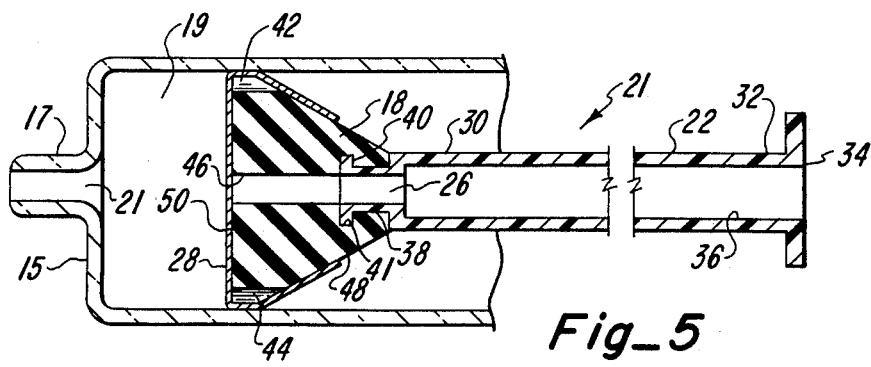
Fig_5

SYRINGE WITH MEANS FOR ALLOWING PASSAGE OF AIR WHILE PREVENTING THE PASSAGE OF BLOOD TO OBTAIN A GAS-FREE BLOOD SAMPLE

CROSS REFERENCE TO RELATED APPLICATIONS

This application is a continuation of U.S. Patent Application Ser. No. 279,453, filed July 1, 1981, now abandoned for a "Syringe With Means for Allowing Passage of Air While Preventing the Passage of Blood".

BACKGROUND OF THE INVENTION

1. Field of Invention

This invention relates generally to syringe devices adapted to collect blood samples. More particularly, the invention relates to syringes capable of collecting blood samples that are purged of any gaseous contaminants.

2. Description of the Prior Art

Syringe devices conventionally include tubular bodies receiving pistons or sealing members connected to plungers. The syringe devices have been adapted to discharge trapped air from an interior chamber, defined by the position of the sealing member, into which chamber a medicament or blood sample is drawn. The structures, and even the specific purposes for removing the air, vary widely.

The time-honored technique for removing air from the interior chamber of a syringe is simply inverting the syringe and squeezing out a portion of the aqueous contents of the interior chamber, presumably with any trapped air. This method is somewhat effective in the preparation of medicaments for injection into a patient, but the indiscriminate discharge of blood in a hospital environment is unsanitary.

There are many prior art syringe devices that utilize some type of vent between the interior chamber and the atmosphere. What differs among the various syringe devices is the manner in which the vent, once formed, is closed at the proper time. An example of a blood-gas syringe device is seen in U.S. Pat. No. 4,206,768 to Bailey, that patent having common ownership with the present application. In the Bailey patent, a vent is formed by a string or thread passed across the sealing member. The string is adapted to be manually wound onto a plunger, sealing the vent, after the blood sample is obtained and the gas has been purged across the sealing member via the vent. The plunger is rotatably connected to the sealing member.

Hollow plungers are one type of structure used for venting air from the interior chamber to ambient pressure. Such a device is seen in U.S. Pat. No. 1,643,531 to Wolf, wherein a sample of medicament is drawn, the air is purged along the hollow plunger, the vent through the plunger is capped, and the syringe is utilized to inject the contents of the syringe. This specific device is not adapted for use in blood-gas analysis because capping the plunger does not seal off air within the plunger from the sample. Wolf also requires capping of the plunger for effective use, as opposed to a self-sealing of the vent at the interior chamber. An extra manual step is required in virtually all of the syringe devices to seal a vent once made.

Filter elements are commonly utilized in syringe devices, primarily for purposes of preventing particulate matter from entering the medicament or the patient. Filters have not been utilized to seal the vent of a blood-gas syringe, though hydrophobic filters, which allow gas to pass until they are wetted, as by blood, are commercially available. Hydrophobic plastic is suggested as a material for an integral plunger-sealing member in U.S. Pat. No. 3,656,480, to Rubricius, but the hydrophobic properties are not necessary for the purposes of the invention.

The prior art does not show a syringe device for obtaining a gas-free blood sample that automatically seals off the blood sample obtained once predetermined conditions are reached. The conditions relate to volume of the blood sample and purging of air associated with the blood sample.

A copending patent application, filed concurrently with the parent application of this application, also assigned to the present assignee, does show a syringe that automatically confines a gas-free blood sample once obtained.

Because of its simplicity, many hospitals and doctors still utilize the expulsion method. A simple, inexpensive syringe device for obtaining a blood-gas sample free of air contamination has just not been available.

OBJECTS AND SUMMARY OF THE INVENTION

The principal object of the present invention is to provide an inexpensively manufactured syringe device for obtaining a gas-free blood sample.

It is a related object of the present invention to provide a syringe device that can be easily operated to obtain a gas-free blood sample.

It is a further related object of the present invention to provide a syringe device for obtaining a gas-free blood sample that automatically seals off the blood sample when a blood sample purged of air is collected.

In accordance with the objects of the invention, a syringe having a hollow, tubular body with an open end and an end wall end having means for connection to an hypodermic needle is provided. The open end of the tubular body receives a plunger rod operatively connected to a piston or sealing member. A passageway or vent is formed along the longitudinal axis of the plunger rod and sealing member, providing for air communication between the ambient environment and an interior chamber of the tubular body, defined as the volume between the sealing member and the end wall. A plurality of grooves are spaced circumferentially around the periphery of the sealing member and provide additional air communication between the interior chamber and the ambient environment. At the interface between the sealing member and the interior chamber, means such as a hydrophobic filter is connected to the sealing member in such a manner as to cover all of the grooves as well as the longitudinal vent for the purpose of sealing the interior chamber from the ambient environment upon contact by blood.

In operation, as blood fills the interior chamber, the means for sealing the interior chamber allows air to be purged through the grooves and the longitudinal vent. At such time as the filter mounted on the sealing member is wetted by contact with the blood, the filter acts to stop passage of blood under the force of human arterial pressure, as well as air, from passing across the filter. Once the interior chamber is completely filled, the hydrophobic filter is completely contacted by the aqueous nature of the blood and sealed against the passage of air across the hydrophobic filter.

BRIEF DESCRIPTION OF THE DRAWINGS

FIG. 1 is a perspective view of the syringe device of the present invention.

FIG. 2 is a section view taken in the plane of line 2—2 of FIG. 1.

FIG. 3 is a section view taken in the plane of line 3—3 of FIG. 1.

FIG. 4 is a side elevational view of the invention shown in FIG. 1 being utilized to obtain a blood sample.

FIG. 5 is a fragmentary longitudinal section view of the syringe of FIG. 1.

DESCRIPTION OF THE PREFERRED EMBODIMENT

A syringe device 10 for obtaining a blood sample under arterial pressure or by aspiration is seen in FIGS. 1 through 5. The blood sample so obtained is uncontaminated by atmospheric air. The gas-free blood sample is ideally suited for blood-gas analysis testing.

The syringe device 10 includes an hypodermic needle 12 which is connected to a cylindrical tubular body 16. The tubular body has a forward extension 17 which frictionally connects in a conventional manner to a hub 13 of the needle or cannula 12. Plunger means 21, including a resilient sealing member 18 and a plunger rod 22, is slideably inserted in the cylindrical body 16 through a circular opening 20 at a trailing end of the cylindrical body. The sealing member is of generally frustoconical shape. The sealing member is operatively connected to the elongated cylindrical plunger rod 22.

The tubular body 16 is formed of a transparent material like glass or disposable plastic, and is of the type that is currently available in large quantities. The extension 17 projects forward from an end wall or end member 15. The extension 17 has a bore 21 which is coaxial with a longitudinal axis of the tubular body 16 (FIG. 5). The bore 21 provides a path from the needle or cannula 12 to an interior chamber 19 of the tubular body 16. The interior chamber is the entire area within the tubular body 16.

The trailing or rearward end of the tubular body 16 has the opening 20 formed therein through which the sealing member 18 can be inserted. The circular opening 20 has a diameter which is substantially equal to the transverse cross sectional inside diameter of the tubular body at any position along the length of the tubular body up to the forward end wall 15. A radially outwardly extending peripheral flange 23 circumscribes the opening 20 at the rearward end of the cylindrical body. The flange 23 facilitates pulling or retracting the plunger rod 22 and attached sealing member 18, or alternatively pushing or inserting the plunger and sealing member along the length of the tubular body 16.

The needle or cannula 12 is also of conventional configuration. A tip 14 is adapted in a conventional manner to be inserted into the artery of a patient 30. At the opposite end from the tip 14 is located the hub 13 which is frictionally connected to the extension 17. Once the tip is inserted into an artery of the patient 30 (FIG. 4), the lumen of the needle 12 allows blood to flow through the needle into the bore 21 of the extension 17 and finally into the interior chamber 19.

The plunger rod 22 is preferably of elongated cylindrical shape having a forward end 30 connected to the sealing member 18, in a manner to be discussed shortly, and a rearward end 32 to which a disc-shaped cap 34 is integrally attached. The rearward end 32 protrudes from the tubular body for manual grasping, to thereby slide the plunger rod and sealing member along the tubular body 16. A plunger rod passageway 36 extends along a longitudinal axis of the plunger rod over the entire length of the plunger rod 22, providing a portion of a vent or air flow passage 26 between the interior chamber 19 and the atmosphere, which vent 26 will be described in detail hereinafter.

The forward end 30 of the plunger rod 22 is connected to the sealing member 18. The forward end includes a relatively narrow neck 38 projecting forwardly along the longitudinal axis of the plunger rod 22. The neck 38 terminates in a lip 40 which extends radially outward from the longitudinal axis of the plunger rod 22 to facilitate connection to the sealing member in a manner to be described hereinafter.

The resilient, generally frustoconically-shaped sealing member 18 is formed or joined to the forward end 30 of the plunger 22 about the neck 38 and lip 40 (FIG. 5). A generally "T" cross sectionally-shaped mating recess 41 is formed interiorly of the sealing member at the rearward end thereof. The recess 41 forms a female-male connection with the neck 38 and lip 40 of the plunger.

The sealing member has a forwardly divergent frustoconical surface 48 extending away from the longitudinal axis of the tubular body 16 and along the length of the tubular body 16 until the surface 48 extends to the interior surface of the tubular body 16. At the leading end of the frustoconical surface 48, the sealing member has a cylindrical surface 42 that extends a relatively short distance forward, compared to the length of the tubular body 16, which cylindrical surface is adapted to slidingly engage the interior surface of the tubular body. The cylindrical surface 42 gives stability to the sealing member 18 as the sealing member slides within the tubular body 16. The circular flat front or leading face 50 extends transversely across the interior of the tubular body. The fact 50 is formed at the forwardmost end of the sealing member 28 and defines an interface with the interior chamber 19. A plurality of longitudinally extending grooves 44 are formed in the sealing member at equal circumferential spacings around the cylindrical surface 42 extending between the flat surface 50 and the divergent surface 48. The grooves 44 provide air flow communication between the interior chamber 19 and the ambient atmosphere. It is seen that the ambient atmosphere pressure is present rearward of the sealing member 18 within the interior of the tubular body 16 itself.

The sealing member 18 also includes a sealing member passageway 46 that is coaxial with the longitudinal axis of the sealing member as well as coaxial with the longitudinal axis of the plunger rod 22. The sealing member passageway 46 is directly aligned through the center of the circular face 50 and with the plunger passageway 36 so as to form the vent 26.

An hydrophobic filter or membrane 28 is disposed across the front face 50 of the sealing member 18 so as to be positioned at the interface between the sealing member 18 and the interior chamber 19. The hydrophobic membrane 28 is joined, as by bonding, to the flat front face 50 of the sealing member. Ideally, the hydrophobic membrane would completely cover the cylindrical surface 42 and be joined to the sealing member 18 along the divergent surface 48. The hydrophobic membrane could be a membrane product such as is manufactured by Gelmann Sciences, Inc. of Ann Arbor, Mich., under the trademark "VERSAPORE 200H", a 0.2 micron material having a water breakthrough pressure of twenty pounds per square inch. Such a membrane 28 establishes passageway sealing means to seal the vent or air flow passage 26 and is impermeable to water as long as the pressure remains below the water breakthrough pressure of twenty pounds per square inch, or nineteen hundred millimeters Hg. Arterial pressures range between ten millimeters Hg and one hundred eighty millimeters Hg, so the likelihood of passage of blood beyond the filter is virtually zero.

In operation, the tip 14 of the needle 12 is inserted into an artery of the patient 30 (FIG. 4). The sealing member 18 has already been located at a preselected position along the length of the tubular body 16, corresponding to a preselected volume of the blood sample to be obtained. The blood pressure of the patient 30 acts to fill the interior chamber 19 with the blood.

As the blood fills the interior chamber 19, it eventually contacts the front face 50 of the sealing member 18, which is covered by the hydrophobic filter 28. The physical properties of the hydrophobic filter are such that air is free to pass the filter until such time as the filter is wetted. Once the blood contacts the filter, the wetted portions of the filter are impervious to air and aqueous matter, like blood. Air cannot cross the interface defined by the filter back into the interior chamber 19 once the filter is wetted.

As the interior chamber 19 continues to fill, displacing air with blood, air is purged through the vent 26 and grooves 44. The grooves 44 are sequentially sealed off from the bottom to the top of the membrane 28. Air transfer cannot occur through the grooves which are covered by rising blood levels. Eventually, the main vent 26 at the sealing member passageway 46 is also sealed off with respect to air and aqueous blood transfer.

As the blood level rises in the interior chamber 19, air continues to pass the hydrophobic membrane 28 through the grooves 44 which are covered by a portion of the hydrophobic filter which have not yet been contacted by the blood. Finally, as the interior chamber 19 completely fills with blood, the last of the air passes through the hydrophobic filter and the grooves 44, at which time the blood seals the hydrophobic membrane, preventing air from re-entering the interior chamber 19 and blood from flowing into the vent 26 or grooves 44.

A preselected dosage of anticoagulant, like sodium heparin, can be placed in the interior chamber 19 prior to the blood sample being drawn. This provides for automatic treatment of the blood sample to prevent coagulation and allow greater time periods for performing blood-gas analysis testing.

Although the present invention has been described with a certain degree of particularity, it is understood tha the present disclosure has been made by way of example and that changes in detail and structure may be made without departing from the spirit thereof.

What is claimed is:

1. A syringe device for obtaining blood samples comprising in combination:
    a tubular body having an interior surface defining an elongated interior chamber, said tubular body having an opening at one end thereof and an end wall at another end thereof, said end wall having an extension protruding therefrom outward of said body, said extension having a bore therethrough, said extension defining means for connecting an hypodermic needle thereto to allow blood to flow from the needle through the bore and into the interior chamber;
    plunger means including an elongated plunger rod having a passageway therethrough and a sealing member having a sealing member passageway therethrough in air flow communication with said plunger rod passageway, said plunger rod being operatively connected to said sealing member, said sealing member having a plurality of longitudinal grooves spaced around a circumference thereof, said grooves contacting said interior surface; and
    an hydrophobic membrane connected to said plunger means for allowing the flow of air through said plunger rod and sealing member passageways, when said hydrophobic membrane is dry, said hydrophobic filter means further preventing the passage of air and blood through said plunger rod and sealing member passageways upon said hydrophobic membrane being contaced by said blood at any pressure less than one hundred eighty millimeters Hg.

2. A syringe device for obtaining a blood sample from a patient under the force of arterial blood pressure, comprising,
    a tubular body having an interior chamber, an end wall at one end of the interior chamber, said end wall being provided with means for connecting a needle to the tubular body and an inlet passage means for communicating blood from the connected needle into said interior chamber;
    plunger means located in said interior chamber, said plunger means including a sealing member which is axially slidable within said chamber, said plunger means being axially spaced from the end wall to provide a blood-receiving space of adjustable volume located between the end wall and the sealing member, said blood-receiving space being radially coextensive with the interior chamber, said plunger means having at least one venting passageway communicating between the blood-receiving space and the ambient environment exterior of the device, said venting passageway being operable to permit gas to flow to the ambient atmosphere from the blood-receiving space;
    passageway sealing means jointed to the plunger means and positioned in the venting passageway, said passageway sealing means when dry being operable to allow gas to flow through said venting passageway, said passageway sealing means when wetted by blood being operable to prevent the flow of blood through said passageway;
    said venting passageway being unobstructed between the sealing means and the ambient environment exterior of the device.

3. A syringe device according to claim 2 wherein the venting passageway includes a plurality of spaced grooves formed in the circumference of said sealing member.

4. A syringe device according to claim 2 wherein the passageway sealing means is operable when wetted by blood to prevent the flow of blood through the passageway at any pressure less than one hundred eighty millimeters Hg.

5. A syringe device according to claim 2 wherein said plunger means includes a rod which projects outwardly from said interior chamber, said venting passageway including a plurality of spaced grooves formed in the circumference of said sealing member, said passageway sealing means being operable when wetted by blood to permit the flow of blood through the passageway at any pressure less than one hundred eighty millimeters Hg.

6. A syringe device according to claim 2 wherein said plunger means includes a rod which projects outwardly from said interior chamber.

7. A syringe device according to claim 6 wherein the venting passageway extends longitudinally through the sealing member and the plunger rod.

8. A syringe device for obtaining a blood sample from a patient under the force of arterial blood pressure, comprising, a tubular body having an interior chamber, an end wall at one end of the interior chamber, said end wall being provided with means for connecting a needle to the tubular body and an inlet passage means for communicating blood from the connected needle into said interior chamber;

plunger means located in said interior chamber, said plunger means including a sealing member which is axially slidable within said chamber to provide a blood-receiving space of adjustable volume located between the end wall and the sealing member, said plunger means having at least one venting passageway communicating between the blood-receiving space and the ambient environment exterior of the device, said venting passageway being operable to permit gas to flow to the ambient atmosphere from the blood-receiving space; and passageway sealing means mounted on the plunger means and positioned in the venting passageway, said passageway sealing means being a hydrophobic filter which, when dry, is operable to allow gas to flow through said venting passageway, said hydrophobic filter when wetted by blood being operable to prevent the flow of blood through said passageway.

9. A syringe device according to claim 8 wherein the venting passageway includes a plurality of spaced grooves formed in the circumference of said sealing member.

10. A syringe device according to claim 8 wherein the passageway sealing means is operable when wetted by blood to prevent the flow of blood through the passageway at any pressure less than one hundred eighty millimeters Hg.

11. A syringe device according to claim 8 wherein said plunger means includes a rod which projects outwardly from said interior chamber, said venting passageway including a plurality of spaced grooves formed in the circumference of said sealing member, said passageway sealing means being operable when wetted by blood to permit the flow of blood through the passageway at any pressure less then one hundred eighty millimeters Hg.

12. A syringe device according to claim 8 wherein said plunger means includes a rod which projects outwardly from said interior chamber.

13. A syringe device according to claim 12 wherein the venting passageway extends longitudinally through the sealing member and the plunger rod.

14. A syringe device for obtaining a blood sample from a patient under the force of arterial blood pressure, comprising, a tubular body having an interior chamber, an end wall at one end of the interior chamber, said end wall being provided with means for connecting a needle to the tubular body and an inlet passage means for communicating blood from the connected needle into said interior chamber;

plunger means located in said interior chamber, said plunger means including a sealing member which is axially slidable within said chamber, said plunger means being axially spaced from the end wall to provide a blood-receiving space of adjustable volume located between the end wall and the sealing member, said blood-receiving space being radially coextensive with the interior chamber, said plunger means having at least one venting passageway communicating between the blood-receiving space and the ambient environment exterior of the device, said venting passageway being operable to permit gas to flow to the ambient atmosphere from the blood-receiving space; and passageway sealing means mounted on the plunger means and positioned in the venting passageway, said passageway sealing means being a hydrophobic filter which, when dry, is operable to allow gas to flow through said venting passageway, said hydrophobic filter when wetted by blood being operable to prevent the flow of blood through said passageway.

15. A syringe device according to claim 14 wherein the venting passageway includes a plurality of spaced grooves formed in the circumference of said sealing member.

16. A syringe device according to claim 14 wherein the passageway sealing means is operable when wetted by blood to prevent the flow of blood through the passageway at any pressure less than one hundred eighty millimeters Hg.

17. A syringe device according to claim 14 wherein said plunger means includes a rod which projects outwardly from said interior chamber, said venting passageway including a plurality of spaced grooves formed in the circumference of said sealing member, said passageway sealing means being operable when wetted by blood to permit the flow of blood through the passageway at any pressure less than one hundred eighty millimeters Hg.

18. A syringe device according to claim 14 wherein said plunger means includes a rod which projects outwardly from said interior chamber.

19. A syringe device according to claim 18 wherein the venting passageway extends longitudinally through the sealing member and the plunger rod.

20. A syringe device for obtaining a blood sample from a patient under the force of arterial blood pressure, comprising, a tubular body having an interior chamber, an end wall at one end of the interior chamber, said end wall being provided with means for connecting a needle to the tubular body and an inlet passage means for communicating blood from the connected needle into said interior chamber;

plunger means located in said interior chamber, said plunger means including a sealing member which is axially slidable within said chamber to provide a blood-receiving space of adjustable volume located between the end wall and the sealing member, said plunger means having at least one venting passageway communicating between the blood-receiving space and the ambient environment exterior of the device, said venting passageway being operable to permit gas to flow to the ambient atmosphere from the blood-receiving space; and passageway sealing means mounted on the plunger means and positioned in the venting passageway, said passageway sealing means when dry being operable to allow gas to flow through said venting passageway, said passageway sealing means when wetted by blood being operable to prevent the flow of blood through said passageway, said device being devoid of any means for interrupting the flow of gas between the passageway sealing means and the ambient environment exterior of the device.

21. A syringe device according to claim 20 wherein the venting passageway includes a plurality of spaced grooves formed in the circumference of said sealing member.

22. A syringe device according to claim 20 wherein the passageway sealing means is operable when wetted by blood to prevent the flow of blood through the passageway at any pressure less than one hundred eighty millimeters Hg.

23. A syringe device according to claim 10 wherein said plunger means includes a rod which projects outwardly from said interior chamber, said venting passageway including a plurality of spaced grooves formed in the circumference of said sealing member, said passageway sealing means being operable when wetted by blood to permit the flow of blood through the passageway at any pressure less than one hundred eighty millimeters Hg.

24. A syringe device according to claim 20 wherein said plunger means includes a rod which projects outwardly from said interior chamber.

25. A syringe device according to claim 24 wherein the venting passageway extends longitudinally through the sealing member and the plunger rod.

26. A method of obtaining a blood sample from a patient with a syringe, said syringe having a tubular body with an interior chamber, a needle communicating with one end of said chamber, a sealing member which is axially movable within the chamber, a plunger rod which is connected to the sealing member and extends outwardly from the tubular body, a venting passageway which extends through the sealing member, and sealing means in the venting passageway which when dry allows blood to flow through the passageway and when wet prevents the flow of blood through the passageway, said method comprising the following steps:
(a) moving said plunger rod to slide said sealing member axially in said interior chamber to a position where gas of a given volume is located between the passageway sealing means and said one end of the chamber,
(b) inserting the needle into the artery of a patient,
(c) flowing blood through the needle and into the chamber under arterial blood pressure,
(d) venting gas from the chamber through the passageway sealing means while blood is flowing into the chamber,
(e) contacting said passageway sealing means with blood when the chamber has received said given volume of blood, thereby sealing said venting passageway,
(f) removing the needle from the patient,
(g) said sealing member being maintained at a stationary position in the chamber during steps (b), (c), (d), (e) and (f).

27. A fluid collection syringe, comprising, in combination:

an elongated hollow housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and gas seal with said sidewall whereby said plunger assembly forms in conjunction with said other end of said housing a fluid receiving chamber within said bore having a volume dependent on the position of said plunger assembly; and said plunger assembly including pressure relief means comprising a bypass element disposed between said plunger and the inside surface of said sidewall for establishing a pressure relief passageway between said chamber and the atmosphere for air trapped in said chamber, said bypass element when dry allowing air to pass through said passageway to enable fluid entering said chamber through said needle member to displace air from said chamber through said passageway, and when wet blocking fluid from passing through said passageway, and remaining at least partially exposed to the interior of said chamber when said chamber is filled with fluid whereby said bypass element is wetted to prevent fluid from leaking from said chamber through said passageway.

28. A fluid sample collection syringe as defined in claim 27 wherein said bypass element is formed of a porous material, which allows the passage of air when dry and blocks the passage of said fluid when wetted by said fluid.

29. A fluid sample collection syringe as defined in claim 27 wherein said plunger includes at least one annular rim portion slidably engaged in gas-sealing relationship to said inside surface of said sidewall and said bypass element is disposed between said rim portion and said sidewall.

30. A syringe as defined in claim 28 wherein said plunger includes at least one annular rim portion slidably engaged in gas-sealing relationship to the inside surface of said sidewall, and said bypass element comprises an annular collar disposed over said rim portion between said rim portion and the interior surface of said sidewall.

31. A syringe for collecting a blood sample from an artery, said syringe comprising, in combination:

an elongated generally cylindrical housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and air seal with said sidewall whereby said plunger assembly forms in conjunction with said other end of said housing a blood receiving chamber within said bore having a volume dependent on the position of said plunger assembly; and said plunger assembly including pressure relief means comprising a bypass element disposed between said plunger and the inside surface of said sidewall for establishing a pressure relief passageway between said chamber and said open end of said bore for air trapped in said chamber, said bypass element when dry allowing the free passage of air from said chamber through said passageway to enable blood entering said chamber under arterial pressure through said needle member to displace air from said chamber, and when wetted by blood blocking the passage of blood through said passageway, and remaining at least partially exposed to the interior of said chamber when said chamber is filled with blood whereby said bypass element is wetted to preclude blood leaking from said chamber through said passageway.

32. A blood sample collection syringe as defined in claim 31 wherein said plunger includes at least one annular rim portion slidably engaged in air-sealed relationship to said inside surface of said sidewall, and said bypass element is disposed between said rim portion and said sidewall.

33. A syringe as defined in claim 31 wherein said plunger includes at least one annular rim portion slidably engaged in air sealing relationship to the inside surface of said sidewall, and said bypass element comprises an annular collar disposed over said rim portion between said rim portion and the interior surface of said sidewall.

34. A blood sample collection syringe as defined in claim 31 wherein said bypass element is formed of a porous material, which allows the passage of gas when dry and blocks the passage of blood when wetted by said blood.

35. A fluid collection syringe comprising, in combination:
an elongated hollow housing having a sidewall defining a central bore, said housing being open at one end to the atmosphere;
a needle member mounted on the other end of said housing, said needle member having a central passageway in communication with said bore;
a plunger assembly slidably mounted within said bore said plunger assembly including a plunger having a rim portion forming at least a partial sliding liquid and gas seal with said sidewall whereby said plunger assembly forms in conjunction with said other end of said housing a fluid receiving chamber within said bore having a volume dependent on the position of said plunger assembly; and
said plunger assembly including pressure relief means comprising an annular bypass element disposed over said rim portion between said rim portion and the inside surface of said sidewall for establishing a pressure relief passageway between said chamber and the atmosphere for gas trapped in said chamber, said bypass element when dry allowing gas to pass from said chamber to allow fluid to enter said chamber through said needle member, and when wet blocking gas from passing from said chamber, and being at least partially exposed to the interior of said chamber whereby when said chamber is filled with fluid said bypass element is wetted to prevent fluid from leaking from the chamber.

36. A syringe for collecting a blood sample from an artery, said syringe comprising, in combination:
an elongated generally cylindrical housing having a sidewall defining a central bore, said housing being open at one end to the atmosphere;
a needle member mounted on the other end of said housing, said needle member having a central passageway in communication with said bore;
a plunger assembly slidably mounted within said bore, said plunger assembly including a plunger having a rim portion forming at least a partial sliding liquid and air seal with side sidewall whereby said plunger assembly forms in conjunction with said other end of said housing a fluid receiving chamber within said bore having a volume dependent on the position of said plunger assembly; and
said plunger assembly including pressure relief means comprising an annular bypass element disposed over said rim portion between said rim portion and the inside surface of said sidewall for establishing a pressure relief passageway between said chamber and said open end of said bore for air trapped in said chamber, said bypass element when dry allowing the free passage of air from said chamber to allow blood to enter said chamber under arterial pressure through said needle assembly and when wetted by said blood blocking the passage of air and blood and being at least partially exposed to the interior of said chamber whereby when said chamber is filled with blood said bypass element is wetted to preclude leaking of blood from said chamber.

37. A fluid collection syringe comprising in combination:
an elongated hollow housing having a sidewall defining a central bore, said housing being open at one end to the atmosphere;
a hollow needle member mounted on the other end of said housing, said needle member having a central passageway in communication with said bore;
a plunger assembly including a plunger slidably mounted within said bore, said plunger assembly forming at least a partial sliding liquid and gas seal with said sidewall whereby said plunger assembly forms in conjunction with said other end of said housing a fluid receiving chamber within said bore having a volume dependent on the position of said plunger assembly; and
said plunger assembly including pressure relief means comprising a bypass element disposed between said plunger and the inside surface of said sidewall for establishing a pressure relief passageway between said chamber and the atmosphere for exhausting air from said chamber upon fluid entering said chamber through said needle member, said pressure relief passageway automatically closing to the passage of fluid without said movement of said plunger upon the chamber becoming filled with fluid.

38. A syringe for collecting a blood sample from an artery, said syringe comprising, in combination:
an elongated generally cylindrical housing having a sidewall defining a central bore, said housing being open at one end to the atmosphere;
a hollow needle member mounted on the other end of said housing, said needle member having a central passageway in communication with said bore;
a plunger assembly including a plunger slidably mounted within said bore, said plunger assembly forming at least a partial sliding liquid and air seal with said sidewall whereby said plunger assembly forms in conjunction with said other end of said housing a blood receiving chamber within said bore having a volume dependent on the position of said plunger assembly; and said plunger assembly including pressure relief means comprising a bypass element disposed between said plunger and the inside surface of said sidewall for establishing a pressure relief passageway between said chamber and the atmosphere for exhausting air from said chamber upon blood entering said chamber through said needle member, said pressure relief passageway automatically closing to passage of blood without movement of said plunger upon said chamber becoming filled with blood.

39. A fluid collection syringe, comprising, in combination:

an elongated hollow housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and gas seal with said sidewall whereby said plunger assembly forms in conjunction with said other end of said housing a fluid receiving chamber within said bore having a volume dependent on the position of said plunger assembly; and said plunger assembly including pressure relief means comprising a bypass element disposed between said plunger and the inside surface of said sidewall, said bypass element when dry allowing air to pass through said bypass element to enable fluid entering said chamber through said needle member to displace air from said chamber through said bypass element, and when wet blocking fluid from passing through said bypass element, and remaining at least partially exposed to the interior of said chamber when said chamber is filled with fluid whereby said bypass element is wetted to prevent fluid from leaking from said chamber through said bypass element.

40. A syringe for collecting a blood sample from an artery, said syringe comprising, in combination:

an elongated generally cylindrical housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and air seal with said sidewall whereby said plunger assembly forms in conjunction with said other end of said housing a blood receiving chamber within said bore having a volume dependent on the position of said plunger assembly; and said plunger assembly including pressure relief means comprising a bypass element disposed between said plunger and the inside surface of said sidewall; said bypass element when dry allowing the free passage of air from said chamber through said bypass element to enable blood entering said chamber under arterial pressure through said needle member to displace air from said chamber, and when wetted by blood blocking the passage of blood through said bypass element, and remaining at least partially exposed to the interior of said chamber when said chamber is filled with blood whereby said bypass element is wetted to preclude blood leaking from said chamber through said bypass element.

41. A fluid collection syringe comprising, in combination:

an elongated hollow housing having a sidewall defining a central bore, said housing being open at one end to the atmosphere;

a needle member mounted on the other end of said housing, said needle member having a central passageway in communication with said bore;

a plunger assembly slidably mounted within said bore said plunger assembly including a plunger having a rim portion forming at least a partial sliding liquid and gas seal with said sidewall whereby said plunger assembly forms in conjunction with said other end of said housing a fluid receiving chamber within said bore having a volume dependent on the position of said plunger assembly; and said plunger assembly including pressure relief means comprising an annular bypass element disposed over said rim portion between said rim portion and the inside surface of said sidewall, said bypass element when dry allowing gas to pass from said chamber to allow fluid to enter said chamber through said needle member, and when wet blocking gas from passing from said chamber, and being at least partially exposed to the interior of said chamber whereby when said chamber is filled with fluid said bypass element is wetted to prevent fluid from leaking from the chamber.

42. A syringe for collecting a blood sample from an artery, said syringe comprising, in combination:

an elongated generally cylindrical housing having a sidewall defining a central bore, said housing being open at one end to the atmosphere;

a needle member mounted on the other end of said housing, said needle member having a central passageway in communication with said bore;

a plunger assembly slidably mounted within said bore, said plunger assembly including a plunger having a rim portion forming at least a partial sliding liquid and air seal with said sidewall whereby said plunger assembly forms in conjunction with said other end of said housing a fluid receiving chamber within said bore having a volume dependent on the position of said plunger assembly; and said plunger assembly including pressure relief means comprising an annular bypass element disposed over said rim portion between said rim portion and the inside surface of sidewall, said bypass element when dry allowing the free passage of air from said chamber to allow blood to enter said chamber under arterial pressure through said needle assembly, and when wetted by said blood blocking the passage of air and blood and being at least partially exposed to the interior of said chamber whereby when said chamber is filled with blood said bypass element is wetted to preclude leaking of blood from said chamber.

43. A fluid collection syringe comprising in combination:

an elongated hollow housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and gas seal with said sidewall whereby said plunger assembly forms in conjunction with said other end of said housing a fluid receiving chamber within said bore having a volume dependent on the position of said plunger assembly; and said plunger assembly including pressure relief means comprising a bypass element disposed between said plunger and the inside surface of said sidewall, said pressure relief means automatically closing to the passage of fluid without movement of said plunger upon the chamber becoming filled with fluid.

44. A syringe for collecting a blood sample from an artery, said syringe comprising, in combination:

an elongated generally cylindrical housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and air seal with said sidewall whereby said plunger assembly forms in conjunction with said other end of said housing a blood receiving chamber within said bore having a volume dependent on the position of said plunger assembly; and said plunger assembly including pressure relief means comprising a bypass element disposed between said plunger and the inside surface of said sidewall, said pressure relief means automatically closing to passage of blood without movement of said plunger upon said chamber becoming filled with blood.

* * * * *

UNITED STATES PATENT AND TRADEMARK OFFICE
CERTIFICATE OF CORRECTION

PATENT NO. : 4,572,210

DATED : February 25, 1986

INVENTOR(S) : Robert J. McKinnon

It is certified that error appears in the above—identified patent and that said Letters Patent is hereby corrected as shown below:

At column 13, line 13 through Column 16, line 20, delete Claims 39 through 44, inclusive.

Signed and Sealed this

First Day of July 1986

[SEAL]

Attest:

DONALD J. QUIGG

Attesting Officer

Commissioner of Patents and Trademarks